United States Patent [19]
Meritt

[11] Patent Number: 5,174,754
[45] Date of Patent: Dec. 29, 1992

[54] SELF-LIGATING, SELF-LOCKING DENTAL BRACKET WITH T-SHAPED ARCHWIRE SLOT

[75] Inventor: Michael A. Meritt, Encinitas, Calif.

[73] Assignee: Johnson & Johnson Consumer Products, Inc., Skillman, N.J.

[21] Appl. No.: 792,516

[22] Filed: Nov. 13, 1991

[51] Int. Cl.⁵ .............................................. A61C 3/00
[52] U.S. Cl. .......................................... 433/8; 433/10
[58] Field of Search ............... 433/5, 8, 9, 10, 11, 433/14, 15, 16, 17, 20

[56] References Cited

U.S. PATENT DOCUMENTS

| | | | |
|---|---|---|---|
| 2,379,011 | 6/1945 | Laskin | 433/8 X |
| 3,423,833 | 1/1969 | Pearlman | 433/8 X |
| 3,464,112 | 9/1969 | Silverman et al. | 433/11 |
| 3,605,233 | 9/1971 | Rosiello | 433/8 X |
| 3,959,880 | 6/1976 | Andrews | 433/11 |
| 4,242,085 | 12/1980 | Wallshein | 433/16 X |
| 4,302,532 | 11/1981 | Wallshein | 433/8 |
| 4,353,692 | 10/1982 | Karrakussoglu | 433/16 |
| 4,521,012 | 6/1985 | Cosby et al. | 482/62 |
| 4,585,413 | 4/1986 | Wool | 433/8 |
| 4,717,146 | 1/1988 | Nohara | 482/62 |
| 4,731,018 | 3/1988 | Adell | 433/20 |
| 4,820,151 | 4/1989 | Pospisil | 433/8 X |
| 4,878,840 | 11/1989 | Reynolds | 433/9 |
| 4,917,602 | 4/1990 | Broussard | 433/8 |
| 4,927,360 | 5/1990 | Pospisil | 433/8 |
| 4,927,362 | 5/1990 | Snead | 433/8 X |
| 4,946,387 | 8/1990 | Adell | 433/20 |
| 5,059,119 | 10/1991 | Snead | 433/8 X |

Primary Examiner—John J. Wilson
Assistant Examiner—Nicholas D. Lucchesi
Attorney, Agent, or Firm—Paul A. Coletti

[57] ABSTRACT

A dental bracket with a T-shaped archwire as described. In addition, it is possible to have a pair of tie wings which lock around the archwire so that the size of the archwire can be reduced, as well as the size of the dental bracket.

8 Claims, 2 Drawing Sheets

SELF-LIGATING, SELF-LOCKING DENTAL BRACKET WITH T-SHAPED ARCHWIRE SLOT

THE FIELD OF THE INVENTION

Generally, this invention relates to self-ligating dental brackets. More specifically, this invention relates to dental brackets which are capable of holding an archwire in place in a locked position. Most specifically, this invention relates to dental brackets which are capable of self-ligating, and self-locking, wherein the archwire slot created in the dental bracket is of a T-shaped cross section.

BACKGROUND OF THE INVENTION

Generally, dental brackets have taken on various shapes and sizes. One of the more popular configurations for dental brackets has been a pair of tie wings separated by an archwire slot. The archwire slot holds an archwire and is capable of fitting the archwire therein so that the archwire may exert a force on the tooth to control movement of that tooth.

Nonetheless, while these previous archwire slot configurations have been quite popular, there are certain perceived drawbacks which present room for improvement. First, there is the need to ligate the archwire in the archwire slot. Previous archwire slots have been quite difficult to ligate.

Second, the aim of dental brackets configurations has been to minimize bracket and archwire size. Thus, any such configuration whereby the archwire may more securely fit into the archwire slot with a smaller size is desirable. Third, with a smaller, self-ligating bracket, it is also desirable to provide a bracket wherein the tie wings contain the typical ball arms or hooks used for ligating bands. Of course, a more typical design is to ligate the band about the tie wings themselves.

Another, fourth, perceived disadvantage of existing standard archwire designs is the archwire slot modulus of elasticity, which is necessarily needed to be quite high in order to exert a force on the tooth after the archwire has been emplaced into the archwire slot. Yet, it is imperative that the archwire resist any tipping, torque or rotational forces. Naturally, while it is important to have an archwire with a high modulus of strength, it is yet again desirable to have an archwire with minimal size. In other words, there previously has been a tension between maintaining size requirements, and also, the strength requirements necessary in a high modulus archwire.

SUMMARY OF THE INVENTION

It is an object of the invention to provide a bracket wherein the archwire is self-ligating.

It is moreover a object of the invention to provide an archwire which maintains a locked position within the archwire slot.

It is yet again another object of the invention to provide a locking mechanism which is deformable in order to accept the archwire, thus reducing the size of the archwire and dental bracket combination.

It is yet again desirable to have an archwire with increased wire modulus of strength.

Finally, it is an object of the invention to provide a dental bracket wherein the size of the archwire and archwire slot are maintained even though the modulus of strength is kept at a high level.

These and other objects of the invention are accomplished in a dental bracket system composed of a dental bracket with a pair of tie wings and an archwire slot. The slot has a pair of walls and a depth generally configured to accept the archwire. The tie wings are deformable at a notch placed on each of the tie wings. This notch, in some instances, may be and spaced about mid-way from the base to the tip of the tie wings. Therefore, when the archwire is placed into the archwire slot, each of the tie wings are displaced or deformed, so that the archwire may pass therethrough and then return to its initial position. When the archwire is placed into the slot, a pair of locking arms on each of the tie wings maintain the archwire in the archwire slot. Preferentially, it may be desirable to have an archwire with a T-shaped cross section when viewed from the end of the dental bracket. In this way, a high modulus of strength is maintained, and yet the size of the archwire can also be minimized.

The invention described will be better understood when taken in conjunction with the attached Detailed Description of the Drawings taken in connection with the Detailed Description of the Invention.

DETAILED DESCRIPTION OF THE DRAWINGS

DETAILED DESCRIPTION OF THE INVENTION

Figure 1:
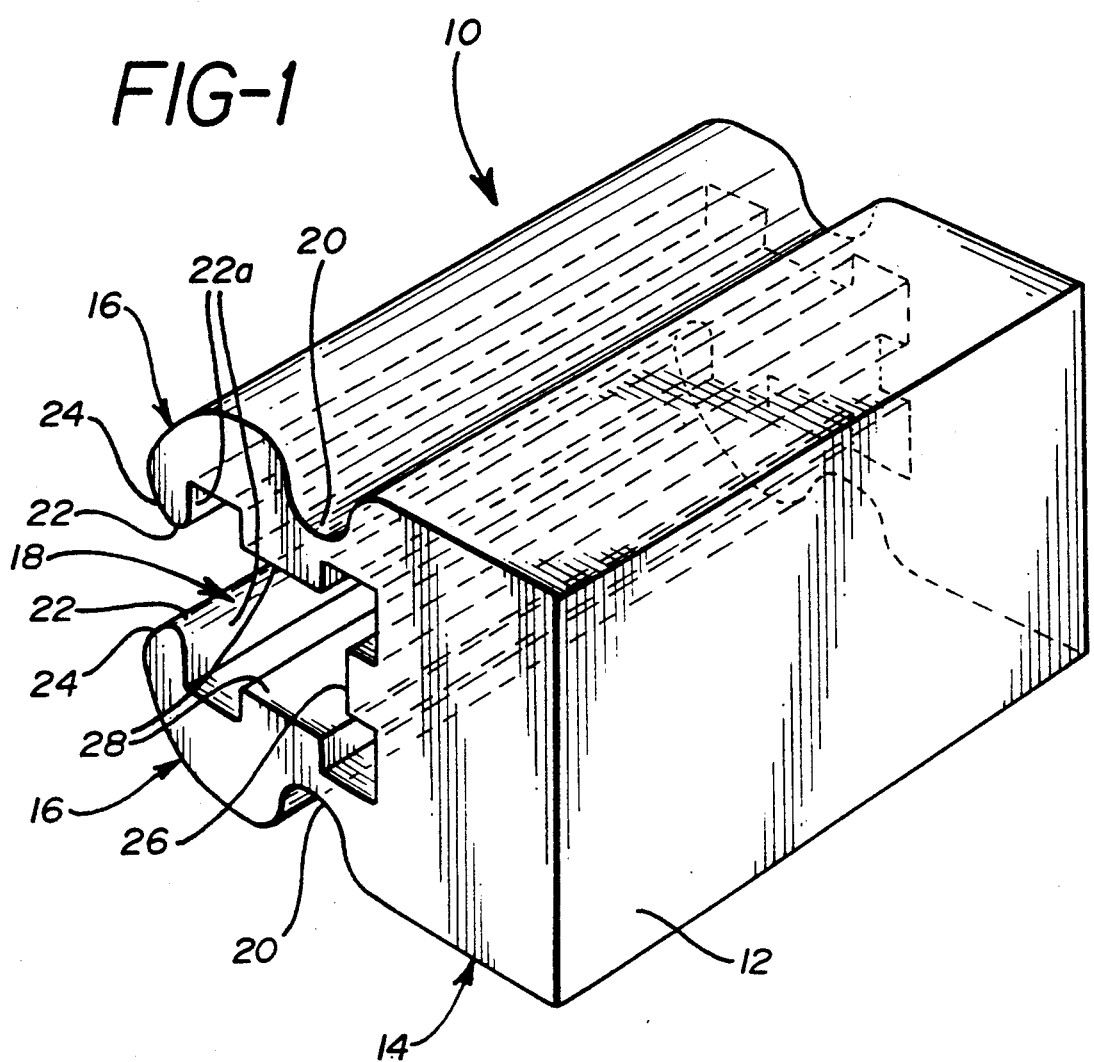
FIG. 1 is a perspective view of a dental bracket of the invention.
Figure 2:
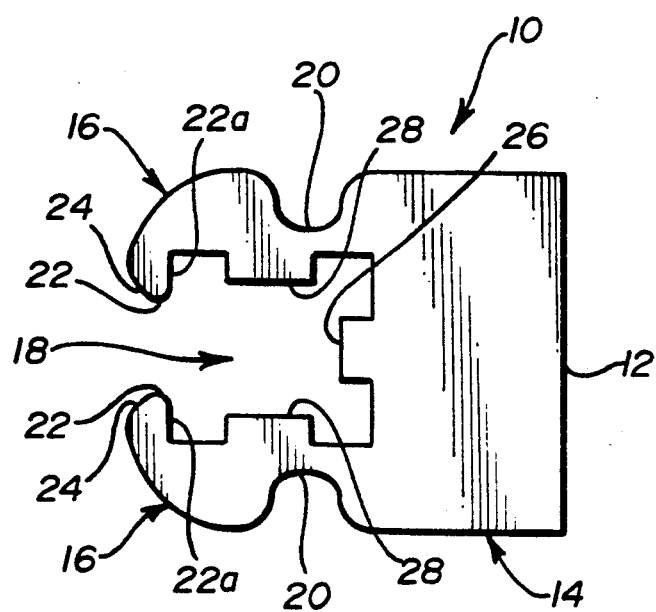
FIG. 2 is a side view of the dental bracket in FIG. 1.

As seen in FIGS. 1 and 2, a dental bracket 10 contains a pad 12 attached to base 14, and a pair of tie wings 16. Each of these tie wings is configured to fit around an archwire slot 18. The tie wings 16 are connected to generally rectangular pad 12 with length of about 0.045" and a depth about 0.030". Thus, the dental bracket 10 is quite compact. Each of the tie wings 16 surrounding the archwire slot 18 would normally be configured with generally parallel walls throughout the length of the tie wing 16. However, as with the configuration of this invention, the tie wings 16 contain two unique features. There is contained from about midway from the base 14, a cantilevered notch 20 on each of the tie wings. Also, there is a locking arm 22 placed at generally perpendicular angles to each of the tie wings 16 at the end of the tie wings 16. It is this unique combination which allows for the placement of an archwire into the archwire slot.

The locking arms 22 are configured so that there is a general interference or press fit between each of the arms 22 and the lateral dimension of the archwire. Thus, when an archwire is ready to be placed within the bracket 10, it first encounters the locking arms 22. Each of the locking arms contain an angular ramp 24 placed on the outside of the arms such that the archwire becomes self-centering.

When the archwire is placed in the bracket 10, the arms 22 displace angularly at the cantilevered notch 20. After the archwire is further into the archwire slot, the arms 22 return to their original position such that they surround the archwire and the archwire held therein. The generally rectangular archwire then encounters pad 26 so that the archwire is held between pad 26, walls 28 and the underside 22a of arms 22.

Thus, many objects of the invention are accomplished. First, it is seen that the archwire is self-ligating. That is, the archwire centers itself on the outer ramps 24 of the locking arms 22. Second, the archwire is locked in place within the archwire slot 18. Because the cantilevered notches 20 have rotated in and out of place, it is possible to reduce the size of the archwire slot so that it is nearly exactly the size of the archwire. Also, the size of the cantilevered notches 20 are such that the walls 28 of the archwire slot 18 may be minimized for size, and yet maintain ability to hold the archwire therein. Because there is no need for maintenance of the archwire, other than the self-ligating and self-locking method as described, the tie wings 16 can contain ball hooks or arms so that force systems or elastomerics may be placed on the bracket. Also, the notches 20 may be used to serve tie wings 16 by anchoring peripheral bands, or to further tie the archwires within the bracket 10, in cases where there is an inability to fully seat the archwire at the beginning of orthodontic treatment.

Because the locking arms 22 have sharp exiting radii, this leads to high forces required for release of the archwire. The archwire slot can therefore resist torque, rotation or tip forces, like those encountered by a typical archwire. The cantilever forming notches 20 in tie wings 16 may be designed so that its height, location, width and depth, are such that it accommodates forces of engagement typical of cast steel, machined steel, plastic, composite materials or the like.

Figure 3:
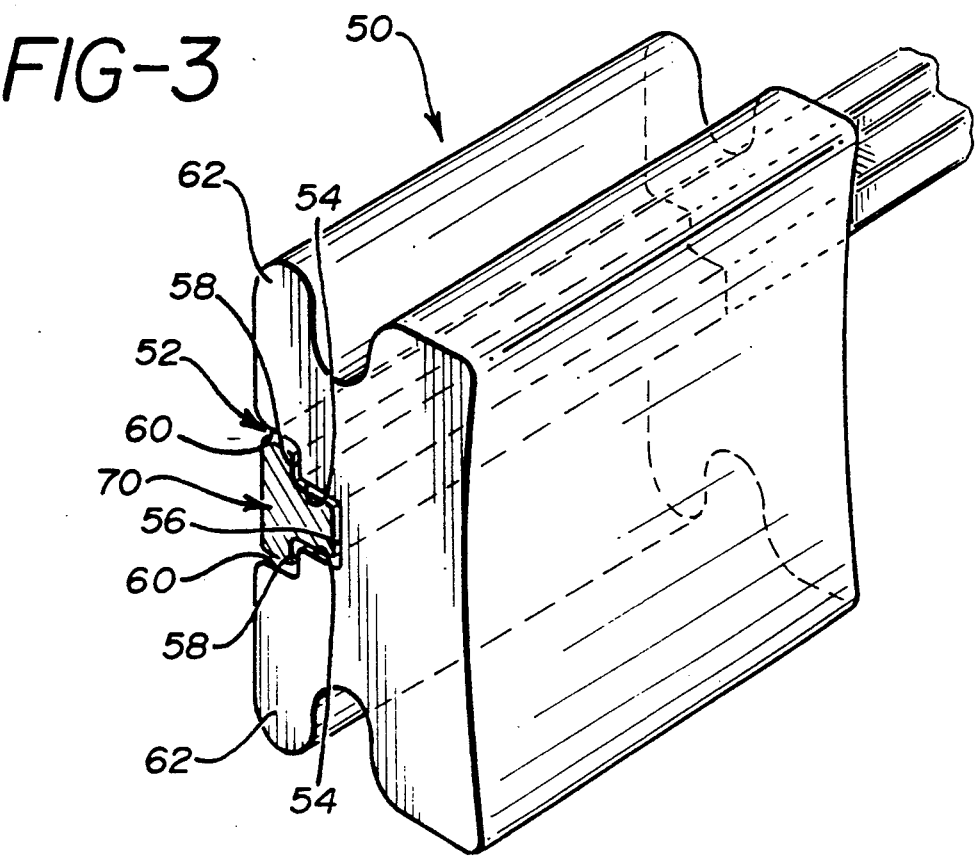
FIG. 3 is a perspective view of an alternate dental bracket of the present invention.
Figure 4:
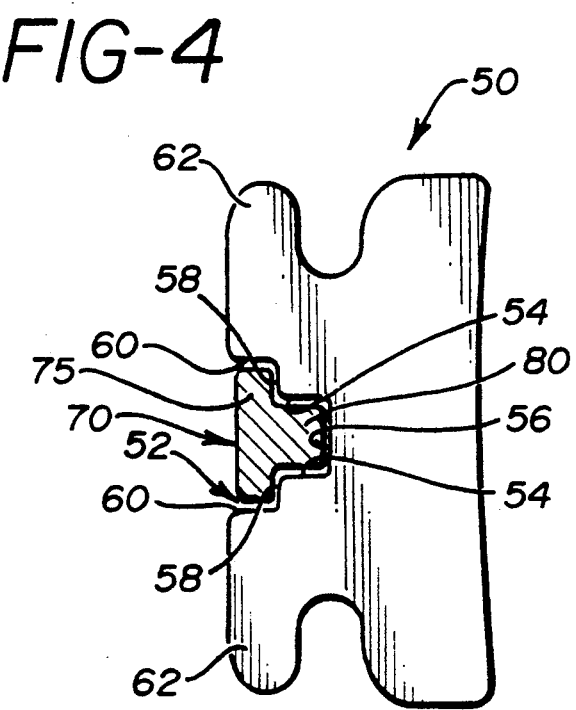
FIG. 4 is an end view of the dental bracket in FIG. 3 with an archwire emplaced therein.
Figure 5:
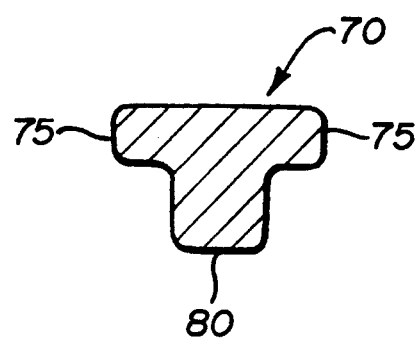
FIG. 5 is a side view of the archwire as placed in FIG. 4 when taken in a cross section along the end of the dental bracket.

As seen in FIGS. 3, 4 and 5, this design may be incorporated with a T-shaped type archwire 70 having cross beams 75 and a vertical beam 80. As seen in FIGS. 3 and 4, the dental bracket 50 has an archwire slot 52 with a pair of perpendicular walls 54 near its base 56. These walls extend in a generally parallel direction, and will form he bases for seating of an archwire. The parallel walls 54 culminate in a pair of shoulders 58 extending at perpendicular directions from the parallel walls 54. Finally, these shoulders 58 culminate in a second pair of parallel walls 60 which are generally perpendicular to the shoulders 58.

Thus, the dental bracket as seen in FIGS. 3 and 4 is capable of accepting an archwire 70 of the cross section as seen in FIGS. 4 and 5. This archwire 70 is capable of maintaining an increased modulus of strength over other composite or fiber optic archwire designs. That is, because the archwire has a larger moment of inertia, its modulus is greater than that of other designs, which must have much larger sizes in order to maintain their high modulus. Of course, the T-beam type shape performs well during the application of tipping, torque or rotational forces and serves as a natural extension to current archwire designs.

It can be realized that this archwire 70 as seen in FIGS. 3, 4 and 5 fits within a typical non-locking bracket 50 containing an archwire slot 52 surrounded by a pair of tie wings 62. However, the bracket 10 as seen in FIGS. 1, 2 and 3 is generally capable of accepting an archwire as seen in FIGS. 3, 4 and 5. In fact, the archwire 70 with a T-shaped cross section is capable of easily being seated onto the locking arms 22 of the tie wings 16 of bracket 10 in FIG. 1 until the cross or horizontal beams 75 of the T-shaped archwire 70 contact the locking arms 22. Thereafter, the tie wings 16 are rotated at cantilevered notches 20, so that the T-shaped archwire 70 is seated well within a archwire slot. It should be appreciated that archwire slot 18 must be modified in bracket 10 to accommodate T-shaped archwire 70. However, tie wings 16 may still contain notches 20 and locking arms 22, such that archwire 70 now ligates and locks in modified archwire slot 18. Thus, the T-shaped archwire 70 results in a enhanced application of both comfort and aesthetics while maintaining a locked condition in a dental bracket 10, as modified.

It is to be realized that the present invention is to be determined from the attached claims and their equivalents.

I claim:

1. A system comprising an archwire and a dental bracket having a pair of tie wings and an archwire slot separating the tie wings, said slot having walls and a depth generally configured to accept said archwire, said tie wings projecting from a base, and each of said tie wings deformable at a notch placed on each of said tie wings, each said notch providing a means for angularly displacing its respective tie wing, wherein when said archwire is placed into said slot, each of said tie wings is initially angularly displaced at said notch and then returns to its original position and wherein said tie wings each contain a locking arm at an end opposite said base, each of said locking arms extending into the space created by said archwire slot, such that said each locking arm is initially displaced in order to allow said archwire into said archwire slot, and wherein said locking arms each contain an outer ramp angled toward said archwire slot such that said archwire is self-centered on said outer ramps when being placed on said locking arms.

2. The system of claim 1 wherein said locking arms prevent movement of said archwire out of said slot after said archwire is placed within said slot.

3. The system of claim 1 wherein said archwire contains a pair of perpendicular arms, such that the cross section of said archwire is "T"-shaped when placed in said bracket and viewed from an end of said bracket.

4. The system of claim 1 wherein said archwire slot contains a pad located on said base, said pad protruding from said base and separated apart from either of said walls.

5. A dental bracket system comprising:
a dental bracket with a base and having a pair of tie wings separated by an archwire slot formed by said tie wings, and having a pair of parallel walls extending from said base, said wall ending at a shoulder placed at generally perpendicular angles to said walls; and
said shoulders extending away from said walls, said shoulders ending in a second pair of parallel walls; and
said second pair of walls placed at generally right angles to said shoulders; and
an archwire for emplacement into said archwire slot;
wherein each of said tie wings is deformable at a notch placed on each of said tie wings, each said notch providing a means for angularly displacing its respective tie wing, wherein when said archwire is placed into said slot, each of said tie wings is initially angularly displaced at said notch and then returns to its original position;

wherein said tie wings each contain a locking arm at an end opposite said base, said locking arms extending into the space created by said archwire slot, such that each said locking arm is initially displaced in order to allow said archwire into said archwire slot; and wherein said locking arms each contain an outer ramp angled toward said archwire slot such that said archwire is self-centered on said outer ramps when being placed on said locking arms.

6. The system of claim 5 wherein said locking arms prevent movement of said archwire out of said slot after said archwire is placed within said slot.

7. The system of claim 5 wherein said archwire contains a pair of perpendicular arms, causing the cross section of said archwire to be "T"-shaped when placed in said bracket and viewed from an end of said bracket.

8. The system of claim 5 wherein said archwire slot contains a pad located on said base, said pad protruding from said base and separated apart from either of said first pair of parallel walls.

* * * * *